US00PP13722P29

(12) United States Plant Patent
Unger

(10) Patent No.: US PP13,722 P2
(45) Date of Patent: Apr. 8, 2003

(54) PLECTRANTHUS PLANT NAMED 'NICO'

(75) Inventor: Michael H. Unger, Rheinfelden (DE)

(73) Assignee: Unger Breeding (DE)

( * ) Notice: Subject to any disclaimer, the term of this patent is extended or adjusted under 35 U.S.C. 154(b) by 0 days.

(21) Appl. No.: 10/113,071

(22) Filed: Apr. 1, 2002

(51) Int. Cl.[7] ..... A01H 5/00
(52) U.S. Cl. ..... Plt./373
(58) Field of Search ..... Plt./263, 373

(56) References Cited

PUBLICATIONS

Andrew Hankey, Plectranthus, Witwatersand National Botanical Garden, South Africa, Apr. 2001.* http://www.saliburygreenhouse.com/annuals.htm.*

All about Nico Plectranthus Http://www.artknapp.com/nico-plectranthus.html.*

* cited by examiner

*Primary Examiner*—Bruce R. Campell
*Assistant Examiner*—W C Haas
(74) *Attorney, Agent, or Firm*—Wood, Phillips, Katz, Clark & Mortimer

(57) ABSTRACT

A new and distinct cultivar of Plectranthus plant named 'Nico', characterized by its upright bushy form, foliage with dark green upper surface and purple lower surface and vigorous growth habit.

2 Drawing Sheets

LATIN NAME OF THE GENUS AND SPECIES OF PLANT CLAIMED

*Plectranthus ambaiuigus.*

VARIETY DENOMINATION

Nico.

BACKGROUND OF INVENTION

The present invention comprises a new and distinct Plectranthus plant, hereinafter referred to by the cultivar name 'Nico'. The new cultivar was discovered as a mutation of an unnamed *Plectranthus ambaiuigus* selection (not patented) in Rheinfelden, Germany in 1998.

Asexual reproduction of the new cultivar by terminal or stem cuttings taken during 2000–2001 at West Chicago, Ill. has demonstrated that the characteristics of the new cultivar as herein described are firmly fixed and retained through successive generations of such asexual propagation.

SUMMARY OF THE INVENTION

It was found that the cultivar of the present invention:

(a) Exhibits an upright bushy form;

(b) forms dark green foliage with dark purple underside; and (c) exhibits a vigorous growth habit.

'Nico' has not been observed under all possible environmental conditions to date. Accordingly, it is possible that the phenotype may vary somewhat with variations in the environment, such as temperature, light intensity, and day length.

When the new cultivar of the present invention is compared to the Plectranthus variety 'Variegata' (not patented) the new cultivar is more compact and upright and has solid green foliage color, whereas 'Variegata' has green and cream variegated foliage.

BRIEF DESCRIPTION OF PHOTOGRAPHS

The accompanying photographs show as nearly true as it is reasonably possible to make the same in color illustrations of this type, typical flower and foliage characteristics of the new cultivar. The plants were grown in a greenhouse at West Chicago, Ill., USA.

The first photograph illustrates the general growth habit of the new cultivar.

The second photograph illustrates a close up of the leaves of the new cultivar.

DETAILED BOTANICAL DESCRIPTION

The chart used in the identification of colors described herein is The R.H.S Colour Chart of The Royal Horticultural Society, London, England. The color values were determined on Jul. 27, 2001 in West Chicago, Ill. The readings were taken between 10:00 and 11:45 p.m. under natural light conditions. The plants were produced from cuttings taken from stock plants and were grown under greenhouse conditions comparable to those used in commercial practice while utilizing a soilless growth medium and maintaining temperatures of approximately 72° F. during the day and approximately 65° F. during the night. Plants used for the following descriptions and measurements were grown for sixteen (16) weeks from rooted cuttings.

Botanical classification: *Plectranthus ambaiuigus* cultivar 'Nico'.

Propagation:

*Type cutting.*—Terminal tip.

*Time to form roots.*—Approximately 21–28 days.

Plant description:

*Crop time.*—Eight to eleven weeks in a 20 cm pot.

*General appearance and form.13* Upright bushy shrub.

*Plant height.*—Approximately 44.3 cm.

*Plant spread.*—Approximately 36.4 cm.

*Number of branches.*—Average of 6 main branches with approximately 13 leaves per branch.

*Branch.*—Shape: Square. Diameter: Approximately 3 mm. Color: 137C. Texture: Densely covered with hairs of darker than 71A, especially along edges.

*Internode length.*—At third node from tip: Approximately 3.5 cm.

Foliage description:

*Form.*—Simple.

*Shape.*—Ovate.

*Margin.*—Crenate.

*Apex.*—Sharply acute.

*Base.*—Attenuate.

*Arrangement.*—Opposite.

*Venation pattern.*—Reticulate.

*Surface.*—Appearance: Shiny. Texture: Upper and lower surfaces: Papillose-hispid.

*Color of young foliage.*—Upper surface: 137A. Lower surface: 71A with 1 mm of 137C along edges.

*Color of mature foliage.*—Upper surface: 137A with midvein of 71A and veins of 137C. Lower surface: 71A with midvein and veins of darker than 71A.

*Size.*—Approximately 9.8 cm in length and approximately 7.3 cm in width.

*Petiole.*—Length: Approximately 2.5 cm. Diameter: Approximately 3 mm. Color: 71B. Texture: Densely covered with hairs of 71A.

Flower description: Flower production was not observed.

Seed production: Seed production was not observed.

Disease resistance: Disease resistance has not been observed.

I claim:

1. A new and distinct cultivar of Plectranthus plant named 'Nico' substantially as herein shown and described, which:

(a) exhibits an upright bushy form;

(b) forms dark green foliage with dark purple under surface; and (c) exhibits a vigorous growth habit.

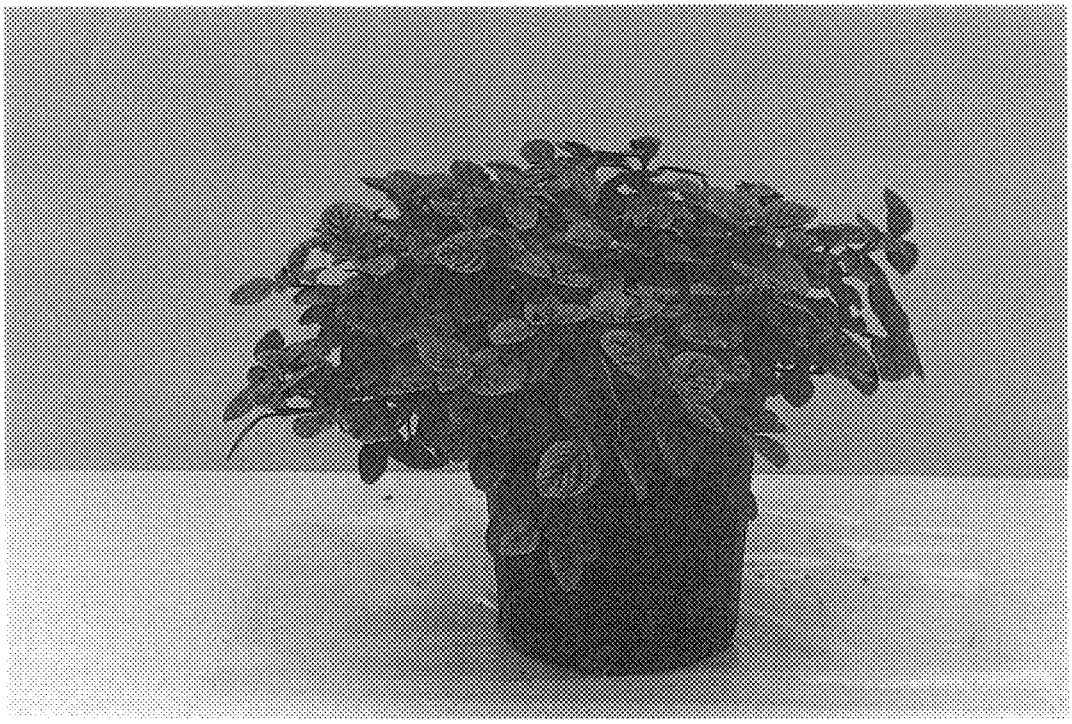

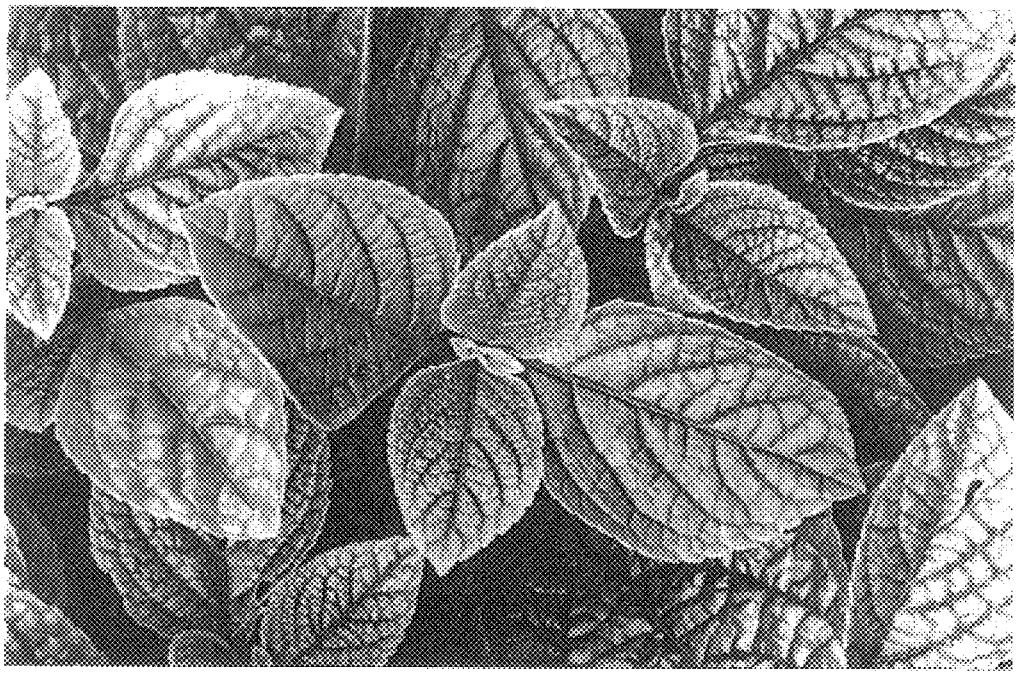

* * * * *